US011813365B2

United States Patent
Langen

(10) Patent No.: US 11,813,365 B2
(45) Date of Patent: Nov. 14, 2023

(54) PASTY PREPARATION FOR FORMING A SEMIRIGID DRESSING

(71) Applicant: Karl Otto Braun GmbH & Co. KG, Wolfstein (DE)

(72) Inventor: Guenter Langen, Wolfstein (DE)

(73) Assignee: KOB GMBH, Wolfstein (DE)

( * ) Notice: Subject to any disclaimer, the term of this patent is extended or adjusted under 35 U.S.C. 154(b) by 803 days.

(21) Appl. No.: 16/649,238

(22) PCT Filed: Sep. 24, 2018

(86) PCT No.: PCT/EP2018/075812
§ 371 (c)(1),
(2) Date: Mar. 20, 2020

(87) PCT Pub. No.: WO2019/063486
PCT Pub. Date: Apr. 4, 2019

(65) Prior Publication Data
US 2020/0246499 A1  Aug. 6, 2020

(30) Foreign Application Priority Data

Sep. 29, 2017  (DE) .................. 10 2017 122 705.9

(51) Int. Cl.
| | |
|---|---|
| *A61L 15/12* | (2006.01) |
| *A61L 15/08* | (2006.01) |
| *A61L 15/10* | (2006.01) |
| *A61L 26/00* | (2006.01) |
| *C07K 14/78* | (2006.01) |
| *C08L 5/06* | (2006.01) |
| *C08L 91/00* | (2006.01) |
| *C08L 5/16* | (2006.01) |

(52) U.S. Cl.
CPC ............. *A61L 15/125* (2013.01); *A61L 15/08* (2013.01); *A61L 15/10* (2013.01); *A61L 26/0004* (2013.01); *A61L 26/0052* (2013.01); *A61L 2300/802* (2013.01); *C07K 14/78* (2013.01); *C08L 5/16* (2013.01); *C08L 91/00* (2013.01)

(58) Field of Classification Search
CPC .... A61L 15/125; A61L 15/08; A61L 26/0004; A61L 26/005; A61L 2300/802; C07K 14/78; C08L 5/16; C08L 91/00
See application file for complete search history.

(56) References Cited

U.S. PATENT DOCUMENTS

| | | | |
|---|---|---|---|
| 4,486,488 A | 12/1984 | Pietsch et al. | |
| 2006/0068024 A1* | 3/2006 | Schroeder | A01N 59/16 424/618 |
| 2013/0085435 A1 | 4/2013 | Murphy et al. | |
| 2015/0246153 A1* | 9/2015 | Ota | A61L 15/18 524/81 |

FOREIGN PATENT DOCUMENTS

| | | |
|---|---|---|
| CH | 282212 A | 8/1952 |
| DE | 3018969 A1 | 11/1981 |
| DE | 10063827 A1 | 7/2002 |
| EP | 0040378 A2 | 11/1981 |
| GB | 949469 | 2/1964 |
| WO | 9002538 A1 | 3/1990 |

OTHER PUBLICATIONS

Pietsch Hanns Dr Dipl-Chem et al. (EP 0040378 A2, 1981, using the Eng. Trans, cited on 1449 filed Feb. 23, 2021). (Year: 1981).*
Jacob Michael (DE 10063827 A1 2002 cited on 1449 filed Feb. 23, 2021, using the Eng. Trans). (Year: 2002).*
Wright Joanne Evelyn et al. (KR 970001498 B1, 1997), Eng Trans. (Year: 1997).*
Wang X (CN 104293495 A), Eng. Trans. (Year: 2015).*
German Search Report of the Priority Application dated Apr. 19, 2018.
European Search Report and Written Opinion from PCT/EP2018/075812 dated Dec. 20, 2018.

* cited by examiner

*Primary Examiner* — Blessing M Fubara
(74) *Attorney, Agent, or Firm* — John Rizvi; John Rizvi, P.A.—The Patent Professor®

(57) ABSTRACT

The invention relates to a pasty preparation for forming a semirigid dressing, said preparation having the following formulation: 30-70% by weight water, 1-10% by weight gelling agent, 10-40% by weight glycerol or polyvalent alcohols, in particular propylene glycol or sorbitol, 0-30% by weight oil, 0.5-5% by weight water-soluble salts, 0.5-2% by weight rheological fillers, and 1-5% adsorbent fillers.

20 Claims, No Drawings

PASTY PREPARATION FOR FORMING A SEMIRIGID DRESSING

This application claims priority to German Patent Application No. 10 2017 122 705.9 filed on Sep. 29, 2017.

The invention relates to a paste-like preparation for forming a semirigid dressing. Such semirigid dressings are known in the prior art in the form of compression, support or relief bandages.

The semirigid dressings used are usually zinc paste dressings, for example in traumatic or sports injuries or tenosynovitis. These have been on the market for many years. Such zinc paste dressings usually consist of zinc oxide, gelatin, glycerol, and water, plus a preservative.

In addition, other synthetic or natural water-soluble swellable polymers can be used, replacing the gelatin.

Such semirigid dressings are usually applied as permanent dressings and are worn for periods ranging from several days to several weeks. The dressings harden over a period of time, forming a comparatively stable shell. However, unlike rigid dressings such as plaster casts, they do not form a completely rigid structure, but retain a degree of deformability.

In standard zinc paste dressings, zinc oxide as a healing-promoting filler, gelatin, and other water-soluble polymers as binders are mixed with water and glycerol. To prolong the shelf life of the mass, organic preservatives, for example para-hydroxybenzoate esters, are additionally added to prevent microbial colonization of the zinc paste dressings, which are stored wet, and to permit an adequate storage time prior to use.

Although skin-friendliness is often cited as an argument for the use of zinc paste dressings, there is a growing number of patients who are prone to skin irritation caused by the preservatives they contain. Such skin irritation and sensitization and allergic reactions jeopardize the desired healing effect of zinc paste bandages if the dressing needs to be removed prematurely because of allergic skin reactions.

Moreover, despite the inclusion of a preservative, wet zinc paste bandages are invariably subject to fungal or bacterial colonization, which is perceptible by an unpleasant odor and unsightly appearance.

EP 0040378 accordingly proposes to provide semirigid zinc paste dressings having a composition of 10 to 35% of zinc oxide, 2 to 15% of cellulose ether, 10 to 35% of water, and 0 to 5% of additives, with preservation achieved by irradiation with high-energy gamma/beta radiation in particular.

A zinc paste bandage disclosed in DE 10063827 A1 is also known from the prior art, and contains
    water,
    gelatin or alginate or hydroxyethyl cellulose or pectin,
    glycerol or sorbitol,
    calcium chloride,
    zinc oxide,
    parabens, and
    0.5% to 5% dexpanthenol
and is said to have skin-care properties.

The object of the present invention is to provide a preparation for a semirigid dressing, and also a semirigid dressing and a corresponding set that does not have the disadvantages mentioned.

The invention achieves this object by means of a paste-like preparation for forming a semirigid dressing comprising the following formulation:
    30% to 70% by weight of water
    1% to 10% by weight of gelling agent
    10% to 40% by weight of glycerol or polyhydric alcohols, especially propylene glycol and/or sorbitol
    0% to 30% by weight of oil
    0.2% to 5% by weight of water-soluble salts
    0.2% to 2% by weight of rheological fillers, and
    1% to 5% by weight of adsorbent fillers.

The invention thus provides a preparation that is, in particular, a zinc-free preparation that, together with a textile carrier material, is able to form a semirigid dressing. This type of semirigid dressing is intended for use as a support or compression bandage on the human or animal body, particularly after sports injuries but after other forms of trauma too, that, after drying, acts as a semirigid dressing in the same way as known zinc paste bandages, but in addition has adsorption properties for chemicals, odors, skin secretions, and microorganisms and can be used as such in dermatological, phlebological or orthopedic treatment.

In particular, the preparation has the following composition:
    40% to 60% by weight of water
    3% to 7% by weight of gelling agent
    15% to 35% by weight of glycerol or polyhydric alcohols, especially propylene glycol and/or sorbitol
    0% to 20% by weight of oil
    0.6% to 2.0% by weight of water-soluble salts
    0.3% to 1.0% by weight of rheological fillers, and
    1.5% to 3.0% by weight of adsorbent fillers.

In addition to water, the paste-like preparation, which is produced by mixing, dissolving and/or homogenizing the components, comprises a gelling agent in the form of water-soluble swellable polymers such as in particular gelatin, starch derivatives, cellulose ethers/esters or mixtures thereof, alginates, guar gum, acacia, pectins and/or agar agar or combinations thereof. The gelling agents serve here as binders and matrix polymers to achieve the desired consistency in a semirigid dressing.

Glycerol or other polyhydric alcohols are employed to modify the hardness and stickiness (adhesion and cohesion) of the gelling agent.

Also included are water-soluble salts, in particular sodium chloride, calcium chloride and/or magnesium chloride. These have the benefit of improving the structural strength and consistency of the paste-like preparation.

In addition, fillers for rheology modification (rheological fillers) may be provided, such as, in particular, aluminum oxide, magnesium oxide and/or silicon dioxide, which adjust the viscosity of the preparation.

The fillers with adsorption properties (adsorbent fillers) that are employed according to the invention are essentially water-insoluble, finely powdered substances that, on account of their high internal surface area, have a high binding capacity for molecules and/or microorganisms (bacteria, yeasts, fungi). For this, it is desirable that the substances have a so-called "BET" surface area of 500 to 1500 $m^2/g$. The BET value is determined in accordance with DIN-ISO 9277:2003-05. Preference is given here to fillers with adsorption properties such as activated carbon, cyclodextrins or cage compounds.

Cage compounds or clathrates or inclusion compounds are understood as being those compounds in which atoms or molecules occupy the structurally defined cavities of a suitable molecular lattice. The "guest molecules" are here fixed in place not by chemical bonds, but by the hollow structure of the "host lattice". Typical examples are solid gas hydrates, for example 8 EÂ•46 $H_2O$ (E=Ar, Kr, Xe, $Cl_2$, $CH_4$ and others), in which E is enclosed in cavities formed through the linking of $(H_2O)_{20}$ dodecahedra by means of hydrogen bonds. Suitable host lattices are also formed by urea, cyclodextrins, hydroquinone, phenol, toluene, and other organic compounds, including some coordination polymers.

Also preferable, should an increase in storage stability be desired, is the use of metals or metal compounds that have an antimicrobial action, such as silver or copper for example. These are preferably added to the formulation in a proportion of 0.05-0.5% by weight. The antimicrobially active metals may be used in particular in elemental form or as a metal compound (salts, oxides).

It is possible to provide in the present manner, a semirigid dressing and a preparation therefor that are both zinc-free and free of organic preservatives and thus skin-friendly. The presence of the adsorbent substances means the preparation can, in particular, be made odorless by giving it adsorption properties for chemicals, odors, skin secretions, sweat and microorganisms. By avoiding organic preservatives, the risk of skin irritation can at the same time be reduced.

These adsorbent fillers were surprisingly found to have preservative properties too, giving rise to good storage stability, in particular for periods of months or years.

This storage stability is a feature in particular of the unhardened state and can if necessary be improved further by adding metals and metal compounds that have an antimicrobial action, such as silver or copper.

As already explained, it is particularly preferable if the preparation is zinc-free. Such a zinc-free preparation is also desirable from the point of view of environmental toxicology, since it means that the dressing is free of heavy metals. Conventional zinc paste bandages contain approx. 5-35% by weight of zinc oxide, which is a significant heavy metal content.

The paste-like preparation is preferably a low- or medium-viscosity paste-like preparation in the form of a glue, a paste or a gel, the viscosity of which is adjustable via the rheological fillers. The viscosity here is preferably 30-6000 mPas at 60° C. This is determined using a Brookfield DV-II+ digital viscometer and spindle 1 (Brookfield, Stoughton, USA).

The adsorbent fillers are dispersed in the paste-like preparation preferably as powders, preferably fine powders.

Oils, for example paraffinic and/or olefinic oils, for example castor oil, may be added, depending on the desired use. This increases the flexibility of the dressing even once it has hardened, although layer adhesion is reduced. Such dressings are referred to as "wet type".

In the production of the dressing, it is particularly preferable if the paste-like preparation is first produced from the individual components including the filler with adsorption properties and, in a second step, a carrier textile is coated/impregnated with this preparation.

Suitable methods that may be employed as the coating technique include dipping, foularding, splashing or pouring, with a homogeneous dispersion of the preparation preferably being applied to the carrier textile.

The fillers with adsorption properties that are used are, in particular, water-insoluble, finely powdered substances that have the following properties:
  essentially water-insoluble, microporous particles,
  water solubility at 20° C.<1 g in 1 l
  internal surface area/BET surface area in the range 500 to 1500 m$^2$/g
  particle fineness/grain size 1 μm to 100 μm (preferably 75% of particles <100 μm, more preferably at least 75% of particles <10 μm)

The size of the particles is determined here in the usual form and refers to the largest possible diameter.

Examples of suitable fillers with appropriate adsorption properties are activated carbon, zeolites and/or finely dispersed silica.

Particular preference is given to using activated carbon as a filler with absorption properties. This imparts a dark gray to black color to the preparation and to the semirigid dressing produced therewith that persists even after the applied semirigid dressing has dried fully on the patient. This black-gray color is less noticeable on dark skin than the bright white conventional zinc paste bandages based on zinc oxide. In addition, the tendency to show dirt is appreciably reduced, which is of benefit when worn for several days. Compliance in the use of dressings is also appreciably improved, particularly in geographic regions in which patients have darker skin tones. However, even without addition of activated carbon and use of other absorbent fillers, the preparation generally has a light yellow to beige color that is likewise less noticeable and less prone to showing dirt.

The invention further relates to a semirigid dressing preparation comprising a strip-form textile carrier to which the preparation is applied. A semirigid dressing preparation is to be understood as meaning the combination of a strip-form textile carrier and a preparation, but which has not yet been applied to a patient. The semirigid dressing preparation is thus the product still in its flexible and wet form. After application to a patient or other exposure to air, evaporation of the liquid, particularly of the water, results in this semirigid dressing preparation hardening within 12-48 h, forming a semirigid dressing on the patient to whom it was applied. The invention also encompasses a semirigid dressing set, with the strip-form textile carrier and the preparation being combined to form a semirigid dressing only immediately before use.

Woven fabrics, knitted fabrics, crocheted fabrics or nonwovens are suitable as textile carriers. It is further particularly preferable if the textile carrier is elastic and in particular if the elasticity is imparted by elastic threads, in particular high-twist cotton threads, in the form of spun or twisted crepe threads, textured polyamide or polyester yarns, rubber threads or polyurethane-elastane threads.

The invention also provides a method for producing a semirigid dressing or a semirigid dressing preparation of the type described above.

It is particularly preferable here if the weight ratio of the textile carrier to the paste-like preparation is in the range from 1:3 to 1:6.

The coated flat material (carrier) is rolled up for storage on a cylindrical reel in a defined length/width, preferably on a plastic core. The plastic core may preferably comprise or consist of polyethylene, polystyrene or polyether. To avoid drying losses due to evaporation, the semirigid dressing preparation is packed inside a hermetically sealed packaging, for example a foil bag, peel pack or thermoformed pack that is impervious to air and water vapor. A suitable example is a three-layer foil laminate in which the first layer consists of a 12 μm thick polyester, the second layer consists of aluminum with a thickness of 6.3 μm, and the third layer consists of a 60 μm polyethylene. In the packaged state, the wet semirigid dressing preparation is in contact with the third layer (polyethylene) of the foil laminate and is protected until the packaging is opened before use. In analogous manner to commercial zinc paste bandages, a storage time of up to three years can be achieved.

The preparation accordingly remains wet prior to use and dries to the desired semirigid configuration through evaporation only once the dressing has been applied. Hardening takes about 1-4 days, preferably 12-24 hours. The dressing retains a residual deformability and residual elasticity compared to rigid dressings such as plaster casts (see definition of semirigid and rigid dressings in Riedel/Triebsch "Verbandstofffibel" [Dressings handbook], 3rd edition 1983, page 115).

It is preferable that the water at least partly evaporates from the preparation within 12-48 h, preferably 12-24 h, as a result of which the dressing is less flexible than before evaporation.

The invention additionally encompasses a semirigid dressing in the applied state, comprising a preparation as described and a strip-form textile carrier to which the preparation is applied, with the semirigid dressing being applied to a patient, in particular being wrapped, and hardening into a semisolid dressing through evaporation of water within 12-48 h. Semisolid bandage or semirigid dressing is to be understood as meaning a bandage that reduces the movement of a joint, but does not completely restrict it.

The invention also relates to a paste-like preparation for forming a semirigid dressing of the above type for use in the treatment of states and conditions selected from the following group: venous thrombosis, swelling caused by injuries or impairment of venous function, chronic venous insufficiency, including venous leg ulcers and phlebedema, thrombophlebitis, phlebothrombosis, fractures of the fibula without deformity, distortions, luxations, tendovaginitis, further treatment after plaster casts, reduction of post-traumatic edema, for rapid decongestion and elimination of chronic edema, phlebitis of deep and superficial veins, post-thrombotic states, aftercare of bone fractures. The invention also encompasses the use of a paste-like preparation of the above type for producing a semirigid dressing for the treatment of venous thrombosis, swelling caused by injuries or impairment of venous function, chronic venous insufficiency, including venous leg ulcers and phlebedema, thrombophlebitis, phlebothrombosis, fractures of the fibula without deformity, distortions, luxations, tendovaginitis, further treatment after plaster casts, reduction of post-traumatic edema, for rapid decongestion and elimination of chronic edema, phlebitis of deep and superficial veins, post-thrombotic states, aftercare of bone fractures.

The invention is elucidated in more detail below with reference to examples.

EXAMPLE 1

Zinc-Free Paste Bandage (Semirigid Dressing Preparation) with Activated Carbon as Adsorbent Filler (Dry Type)

The paste-like preparation according to the invention is produced according to the following formulation:

| | |
|---|---|
| Comp. A 490 g of demineralized water | (equivalent to 56.9%) |
| Comp. B 37.5 g of carboxymethyl cellulose | (equivalent to 4.4%) |
| Comp. C 10.0 g of gelatin | (equivalent to 1.1%) |
| Comp. D 300 g of glycerol 85% | (equivalent to 34.8%) |
| Comp. E 6.7 g of calcium chloride dihydrate | (equivalent to 0.8%) |
| Comp. F 17.0 g of activated carbon | (equivalent to 2.0%) |
| Total amount 861.2 g | (equivalent to 100%) |

A heatable vessel (volume 2000 ml) fitted with a stirrer unit is charged with the specified amount of demineralized water (comp. A) and heated to 40° C. Component B as a further gelling agent (Walocel CRT 30 GA, manufacturer Dow, Walsrode) in powder form is added slowly at medium stirrer speed (1000 rpm) and the mixture is stirred for 30 minutes until a clear solution has formed. Component C (Gelita pharma-grade gelatin Gold Extra 180 Bloom, manufacturer Gelita AG, Eberbach) in powder form is then added slowly and the mixture is again stirred for 30 minutes until a clear solution has formed. This is followed by the successive addition of component D (pharma-grade glycerol 85%, manufacturer Biesterfeld, Friedrichsthal) and E, as water-soluble salt, (calcium chloride dihydrate, manufacturer Merck, Darmstadt). The mixture is up to this point a light yellow-beige color. Finally, the activated carbon (Carbopal SC 11 PG, manufacturer Donaucarbon, Frankfurt) in powder form is added and stirred in until a homogeneous deep black paste has formed. This paste is cooled to 30° C. with constant stirring (speed 500 rpm) and used in this form for coating the carrier textile. The paste is optically homogeneous in appearance. No sedimentation is discernible within 3 days.

The mass from example 1 is stable to storage for several weeks (4-8) without microbial colonization (surface covering of mold) being visible or noticeable through an odor of decomposition.

To produce the semirigid dressing (paste dressing) according to the invention or a semirigid dressing preparation, the carrier fabric specified below is used, which is produced on a ribbon loom with a rapier weft insertion device:

Longitudinally elastic gauze bandage according to DIN 61634 with firm selvages, type 564, width 10 cm:

| | |
|---|---|
| Material composition of the fabric | 71% viscose, 29% polyamide, plain weave |
| Warp thread 1/warp thread 2 | 17 tex viscose/78 dtex f 17 × 2 textured polyamide |
| Thread count of warp thread 1/warp thread 2 | 56/56 per 10 cm width |
| Weft | 17 dtex viscose |
| Weft density | 36 double weft per 10 cm stretched (DIN 61632) |
| Weight per unit area stretched | 32 g/m² (DIN 61632) |
| Elasticity | in longitudinal direction (warp direction) |
| Stretch/recovery according to DIN 61632 | 140%/99% |
| Air permeability DIN 53887 | 5000-7000 l/m² sec |

Coating is carried out using a 2-roll foulard from Mathis, Oberhasli (CH), wherein one roll is driven and may be pressed against the other by means of compressed air. The paste is fed into the nip (gusset) of the two horizontally arranged rubber rollers (diameter 100 mm, width 300 mm, rubber Shore hardness 60°). The air pressure is then reduced such that there is a visible gap (0.5-1 mm) between the rollers. The elastic fabric strip is fed from above through the paste in the gusset into the nip until it is drawn through by the drive of the rollers. The textile strip coated with the paste then emerges below and is wound onto a cardboard tube serving as the roll core, keeping tension to a minimum and the edges as straight as possible. The contact pressure and gap are set such that the weight ratio of textile to paste is in the range from 1:3 to 1:6, depending on the desired paste content. On reaching the desired length, the coated strip is cut off and the end of the bandage is laid flush on the cylindrical reel. The gray-black paste dressing thus produced has the following characteristics:

| | |
|---|---|
| Color | Gray-black |
| Bandage width | 10.0 cm |
| Bandage diameter (on 30 mm core) | 74 mm |
| Bandage length unstretched (DIN 61632) | 610 cm |
| Bandage length stretched (DIN 61632) | 1020 cm |
| Stretch (DIN 61632) | 67% |
| Bandage weight (without core) | 188 g |
| Proportion by weight of textile | 32 g |
| Proportion by weight of preparation | 156 g |
| Weight ratio textile/preparation | 1:4.9 |

In analogous manner to the known zinc paste bandages, the semirigid dressing preparation according to example 1 is hermetically sealed inside a tubular bag packaging made from a three-layer barrier film that is impervious to air and water vapor (manufactured for example by Heyne & Penke, Dassel) and stored therein until use. Even after several weeks, the bandage remains usable and free of microbial colonization.

For use, the tubular bag packaging is opened and the bandage is wound around the leg of the subject as a lower-leg compression bandage with 50% overlap and avoiding wrinkles. The layers stick to one another firmly, including in particular the bandage end on the substrate. The semirigid dressing preparation hardens to a semirigid dressing over the course of 12 to 24 hours, with the dressing feeling slightly rough and dry on the outside. The layers are stuck together even more firmly after drying and the gray-black color is a little lighter in appearance. The subject feels comfortable with the dressing and does not perceive any odors, even after wearing it for several days.

EXAMPLE 2

Zinc-Free Paste Bandage with Silicon Dioxide/Activated Carbon as Adsorbent Filler (Wet Type)

The paste-like preparation according to the invention is produced according to the following formulation:

| | |
|---|---|
| Comp. A 490 g of demineralized water | (equivalent to 56.7%) |
| Comp. B 37.5 g of carboxymethyl cellulose | (equivalent to 4.3%) |
| Comp. C 10.0 g of gelatin | (equivalent to 1.1%) |
| Comp. D 150 g of glycerol 85% | (equivalent to 17.4%) |
| Comp. E 150 g of castor oil | (equivalent to 17.4%) |
| Comp. F 6.7 g of calcium chloride dihydrate | (equivalent to 0.8%) |
| Comp. G 2.5 g of silicon dioxide | (equivalent to 0.3%) |
| Comp. H 17.0 g of activated carbon | (equivalent to 2.0%) |
| Total amount 863.7 g | (equivalent to 100%) |

Production is carried out in analogous manner to the procedure described in example 1, using the same chemicals in the sequence of components A to H. Used here as a new component E is castor oil (pharma-grade castor oil, manufacturer Kirsch Pharma, Salzgitter). Castor oil subsequently serves as a moisturizer and softener in the dressing, which is why this type of paste bandage (semirigid dressing) is referred to as "wet type". In addition to activated carbon, silicon dioxide (Aerosil 200, manufacturer Degussa, Frankfurt) is added as a further filler with adsorption properties, as component G. Prior to mixing in component G, the mass is a milky gray-white. After adding the activated carbon (component H), a homogeneous deep black paste is formed, which is cooled to 30° C. with constant stirring at a speed of 550 rpm and is used in this form for coating the carrier textile. The paste is optically homogeneous in appearance; no sedimentation is discernible within 3 days.

The mass from example 2 is likewise stable to storage for several weeks (4-8 weeks) without microbial colonization (surface covering of mold) being visible or noticeable through an odor of decomposition.

Coating is carried out in analogous manner to the description in example 1. In this case, a gray-black paste bandage is again produced as a semirigid dressing preparation that has the following characteristics:

| | |
|---|---|
| Color | Gray-black |
| Bandage width | 10.0 cm |
| Bandage diameter (on 30 mm core) | 7 3 mm |
| Bandage length unstretched (DIN 61632) | 615 cm |
| Bandage length stretched (DIN 61632) | 990 cm |
| Stretch (DIN 61632) | 61% |
| Bandage weight (without core) | 178 g |
| Proportion by weight of textile | 31.5 g |
| Proportion by weight of preparation | 146.5 g |
| Weight ratio textile/preparation | 1:4.6 |

In analogous manner to example 1, the bandage is hermetically sealed inside a tubular bag packaging made of a suitable barrier film that is impervious to air and water vapor and stored therein until use. Even after several weeks, the bandage remains usable and free of microbial colonization.

For use, the tubular bag packaging is opened and the bandage is wound around the leg of the subject as a lower-leg compression bandage with 50% overlap and avoiding wrinkles. In this case, the castor oil content means that the layers stick to one another less firmly, including in particular the end of the bandage/dressing. The dressing hardens into a semirigid dressing over the course of 12 to 24 hours and in this case, the bandage feels smooth, creamy, and wet on the outside. After drying, the layers are stuck to one another less firmly than in example 1, which is altogether desirable for the wet type. The gray-black color is in turn a little lighter in appearance. The subject feels comfortable with the dressing and does not perceive any odors, even after wearing it for several days.

EXAMPLE 3

Comparative Example: Zinc-Containing Paste Bandage without Adsorbent Filler (Dry Type)

As a comparative example, a zinc-containing paste-like preparation without addition of fillers with adsorbent properties is produced according to the following formulation:

| | |
|---|---|
| Comp. A 490 g of demineralized water | (equivalent to 49.3%) |
| Comp. B 37.5 g of carboxymethyl cellulose | (equivalent to 3.8%) |
| Comp. C 10.0 g of gelatin | (equivalent to 1.0%) |
| Comp. D 300 g of glycerol 85% | (equivalent to 30.2%) |
| Comp. E 6.7 g of calcium chloride dihydrate | (equivalent to 0.7%) |
| Comp. F 150 g of zinc oxide | (equivalent to 15.0%) |
| Total amount 994.2 g | (equivalent to 100%) |

Production is carried out in analogous manner to the procedure described in example 1, using the same chemicals in the sequence of components A to E. Zinc oxide (pharma-grade zinc oxide, manufacturer Briggemann KG, Heilbronn) is added as component F. This bright white paste is cooled to 30° C. with constant stirring (speed 500 rpm) and used in this form for coating the carrier textile. The paste is optically homogeneous in appearance; after 1 day slight sedimentation in the form of a zinc oxide sediment is discernible. A coating of mold develops after 1-2 weeks on the mass in the comparative example, which indicates microbial colonization. This is also evidenced by an intense putrid odor of decomposition.

Coating the textile carrier to produce the finished paste bandage (semirigid dressing preparation) was therefore omitted.

The invention claimed is:

1. A paste-like preparation for forming a semirigid dressing comprising the following formulation:
   30-70% by weight of water,
   1-10% by weight of gelling agent,
   10-40% by weight of glycerol or polyhydric alcohols,
   0-30% by weight of oil,
   0.2-5% by weight of water-soluble salts,
   0.2-2% by weight of rheological fillers, and
   1-5% by weight of adsorbent fillers,
   wherein the preparation is a zinc-free preparation.

2. The preparation as claimed in claim 1, wherein the formulation further contains 0.05-0.5% by weight of metals and/or metal compounds that have an antimicrobial action.

3. The preparation, of claim 2, wherein metals or metal compounds that have an antimicrobial action are silver and/or copper.

4. The preparation as claimed in claim 1, wherein the gelling agent is a water-soluble polymer selected from the group consisting of gelatin, starch derivatives, cellulose derivatives, alginates, acacia, agar, and mixtures thereof.

5. The preparation of claim 1, wherein the oil is a paraffinic and/or olefinic oil.

6. The preparation of claim 1, wherein the rheological fillers are selected from the group consisting of aluminum oxide, magnesium oxide, silicon dioxide, and mixtures thereof.

7. The preparation claims of claim 1, wherein the adsorbent fillers are selected from the group consisting of activated carbon, cyclodextrin, finely dispersed silica, and mixtures thereof.

8. The preparation of claim 1, wherein the preparation has a viscosity of 30-6000 mPas at 60° C.

9. The preparation of claim 1, wherein the adsorbent fillers are dispersed in powder form in the paste-like preparation.

10. The preparation of claim 1, wherein it is yellowish, beige, gray or black in color.

11. A semirigid dressing set consisting of a strip-form textile carrier and a preparation of claim 1.

12. A method of treating states and conditions selected from the group consisting of venous thrombosis, swelling caused by injuries or impairment of venous function, chronic venous insufficiency, including venous leg ulcers and phlebedema, thrombophlebitis, phlebothrombosis, fractures of the fibula without deformity, distortions, luxations, tendovaginitis, further treatment after plaster casts, reduction of post-traumatic edema, for rapid decongestion and elimination of chronic edema, phlebitis of deep and superficial veins, post-thrombotic states, aftercare of bone fractures, and mixtures thereof, wherein the method comprises employing the paste-like preparation for forming a semirigid dressing of claim 1.

13. A semirigid dressing preparation comprising a strip-form textile carrier to which the preparation of claim 1 is applied.

14. The semirigid dressing preparation as claimed in claim 13, wherein the textile carrier is coated or impregnated or coatable or impregnatable with the preparation.

15. The semirigid dressing preparation of claim 13, wherein the textile carrier is selected from the group consisting of a woven fabric, knitted fabric, crocheted fabric or nonwoven fabric.

16. The semirigid dressing preparation or semirigid dressing set as claimed in claim 13, wherein the textile carrier is elastic.

17. The semirigid dressing preparation as claimed in claim 13, wherein the weight ratio of carrier to preparation is from 1:3 to 1:6.

18. A compression, support or relief bandage comprising the semirigid dressing preparation of claim 13.

19. A method for producing a semirigid dressing preparation of claim 13, wherein the preparation is applied to one or both sides of the strip-form textile carrier material.

20. A semirigid dressing obtained from a semirigid dressing preparation of claim 13, wherein the water at least partly evaporates from the preparation within 12-48 h as a result of which the bandage is less flexible than prior to evaporation.

* * * * *